United States Patent
Reiner

(10) Patent No.: US 7,593,549 B2
(45) Date of Patent: Sep. 22, 2009

(54) APPARATUS AND METHOD FOR UTILIZING BIOMETRICS IN MEDICAL APPLICATIONS

(76) Inventor: Bruce Reiner, 6 Greenleaf La., Seaford, DE (US) 19973

( * ) Notice: Subject to any disclaimer, the term of this patent is extended or adjusted under 35 U.S.C. 154(b) by 0 days.

(21) Appl. No.: 11/790,843

(22) Filed: Apr. 27, 2007

(65) Prior Publication Data

US 2007/0258626 A1  Nov. 8, 2007

Related U.S. Application Data

(60) Provisional application No. 60/795,199, filed on Apr. 27, 2006.

(51) Int. Cl.
G06K 9/00 (2006.01)

(52) U.S. Cl. .......................... 382/115; 382/218; 705/3; 713/168; 713/186

(58) Field of Classification Search ................. 382/115, 382/116, 117, 118, 119, 124; 705/2, 3; 713/168, 713/186

See application file for complete search history.

(56) References Cited

U.S. PATENT DOCUMENTS

| | | | |
|---|---|---|---|
| 5,802,199 A * | 9/1998 | Pare et al. .................... | 382/115 |
| 5,867,812 A | 2/1999 | Sassano | |
| 5,876,926 A | 3/1999 | Beecham | |
| 5,912,818 A | 6/1999 | McGrady et al. | |
| 5,924,074 A | 7/1999 | Evans | |
| 5,930,804 A | 7/1999 | Yu et al. | |
| 6,031,910 A | 2/2000 | Deindl et al. | |
| 6,044,349 A | 3/2000 | Tolopka et al. | |
| 6,070,141 A | 5/2000 | Houvener et al. | |
| 6,081,750 A | 6/2000 | Hoffberg et al. | |
| 6,662,166 B2 * | 12/2003 | Pare et al. ...................... | 705/39 |
| 6,851,054 B2 * | 2/2005 | Wheeler et al. .............. | 713/176 |
| 7,310,651 B2 * | 12/2007 | Dave et al. ............... | 707/104.1 |
| 2002/0010679 A1 | 1/2002 | Felsher | |
| 2003/0028811 A1 * | 2/2003 | Walker et al. ................ | 713/202 |
| 2003/0088441 A1 | 5/2003 | McNerney | |
| 2003/0142855 A1 * | 7/2003 | Kuo et al. .................... | 382/119 |
| 2003/0225693 A1 * | 12/2003 | Ballard et al. .................. | 705/42 |
| 2004/0054923 A1 | 3/2004 | Seago et al. | |
| 2004/0117215 A1 | 6/2004 | Marchosky | |
| 2004/0122709 A1 | 6/2004 | Avinash et al. | |
| 2004/0186357 A1 * | 9/2004 | Soderberg et al. ........... | 600/300 |
| 2005/0101841 A9 | 5/2005 | Kaylor et al. | |
| 2005/0203771 A1 | 9/2005 | Achan | |
| 2006/0026043 A1 * | 2/2006 | Schneider et al. .............. | 705/3 |

(Continued)

*Primary Examiner*—Gregory M Desire
(74) *Attorney, Agent, or Firm*—Jean C. Edwards, Esq.; Akerman Senterfitt

(57) ABSTRACT

In the present invention, the user will sign onto a system, utilizing a biometrics authentication or identification procedure. Once authentication and identification takes place, local, regional, and centralized medical databases can be automatically queried using the identification-specific biometrics signature. All data intrinsic to the medical procedure or examination being performed will be automatically tagged and downloaded into that specific patient's electronic medical database. At the same time, that patient's medical database is queried to provide all historical data relevant to the medical examination or procedure being performed to assist with planning, protocol, and analysis of the data being collected. The biometrics authentication can be performed at patient intake, at an imaging device, at a pharmacy, or in the operating room, to ensure that the personnel and the patient are correctly identified before any procedure is performed or drug administered.

62 Claims, 7 Drawing Sheets

U.S. PATENT DOCUMENTS

| | | |
|---|---|---|
| 2006/0098847 A1* | 5/2006 | Takahashi .................. 382/115 |
| 2006/0100906 A1* | 5/2006 | Sweetser ....................... 705/2 |
| 2006/0173712 A1 | 8/2006 | Joubert |
| 2006/0229909 A1 | 10/2006 | Kaila et al. |
| 2006/0293921 A1 | 12/2006 | McCarthy et al. |
| 2007/0005396 A1* | 1/2007 | Lee ............................... 705/3 |
| 2007/0027715 A1 | 2/2007 | Gropper et al. |
| 2007/0041620 A1* | 2/2007 | Ito ............................. 382/115 |
| 2007/0055552 A1 | 3/2007 | St. Clair et al. |
| 2008/0097786 A1* | 4/2008 | Sachdeva ....................... 705/2 |
| 2008/0162352 A1* | 7/2008 | Gizewski ..................... 705/50 |

* cited by examiner

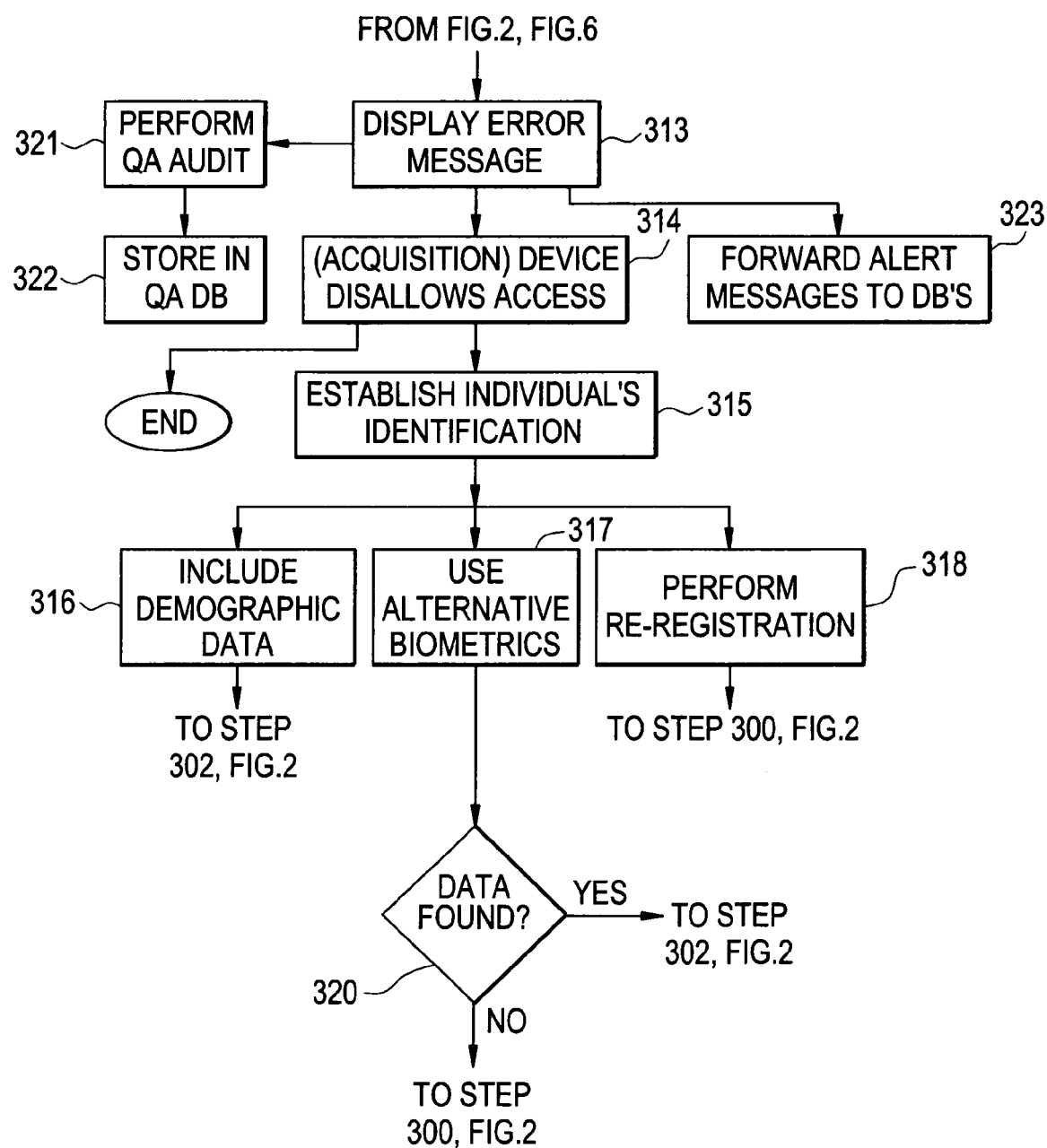

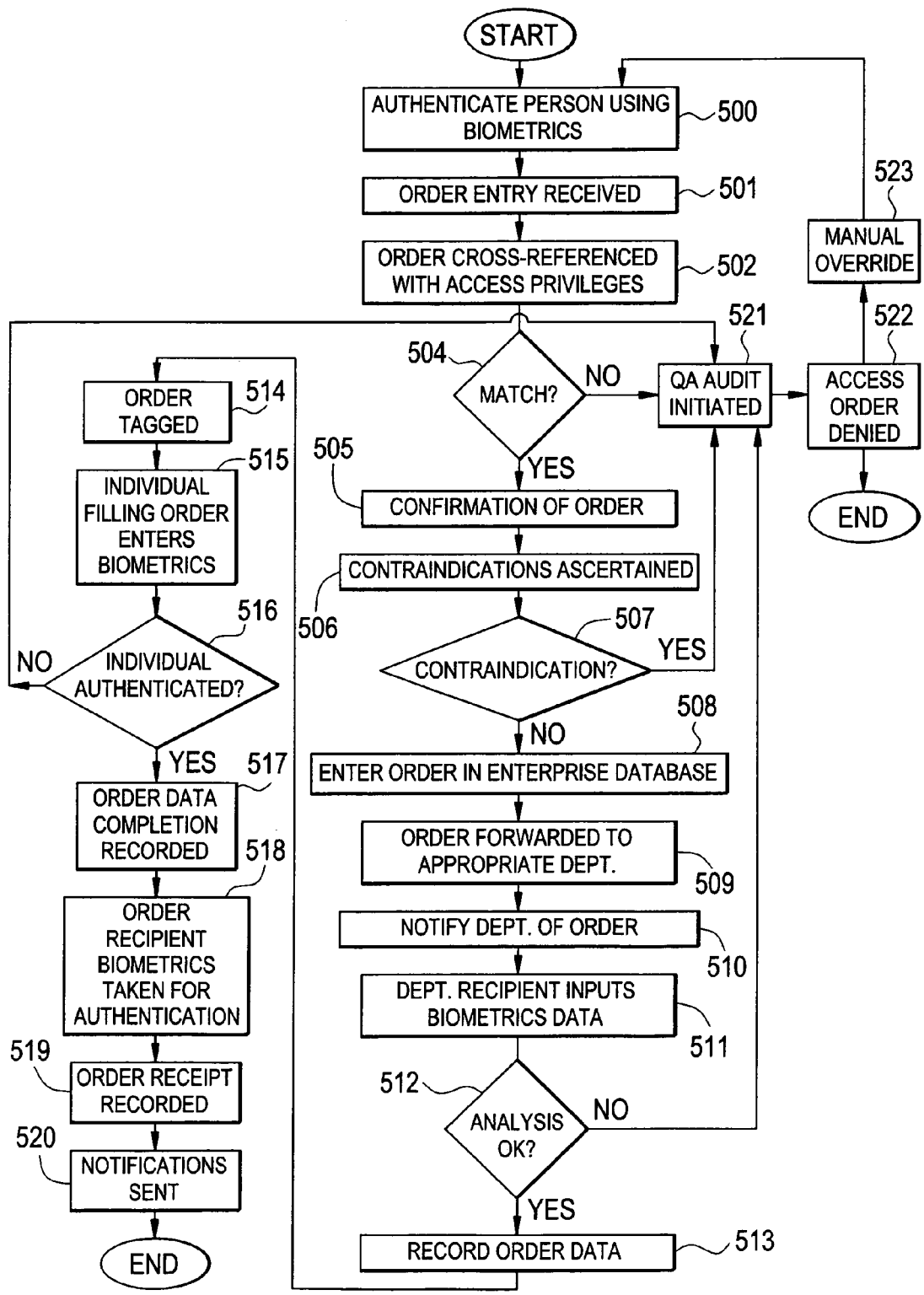

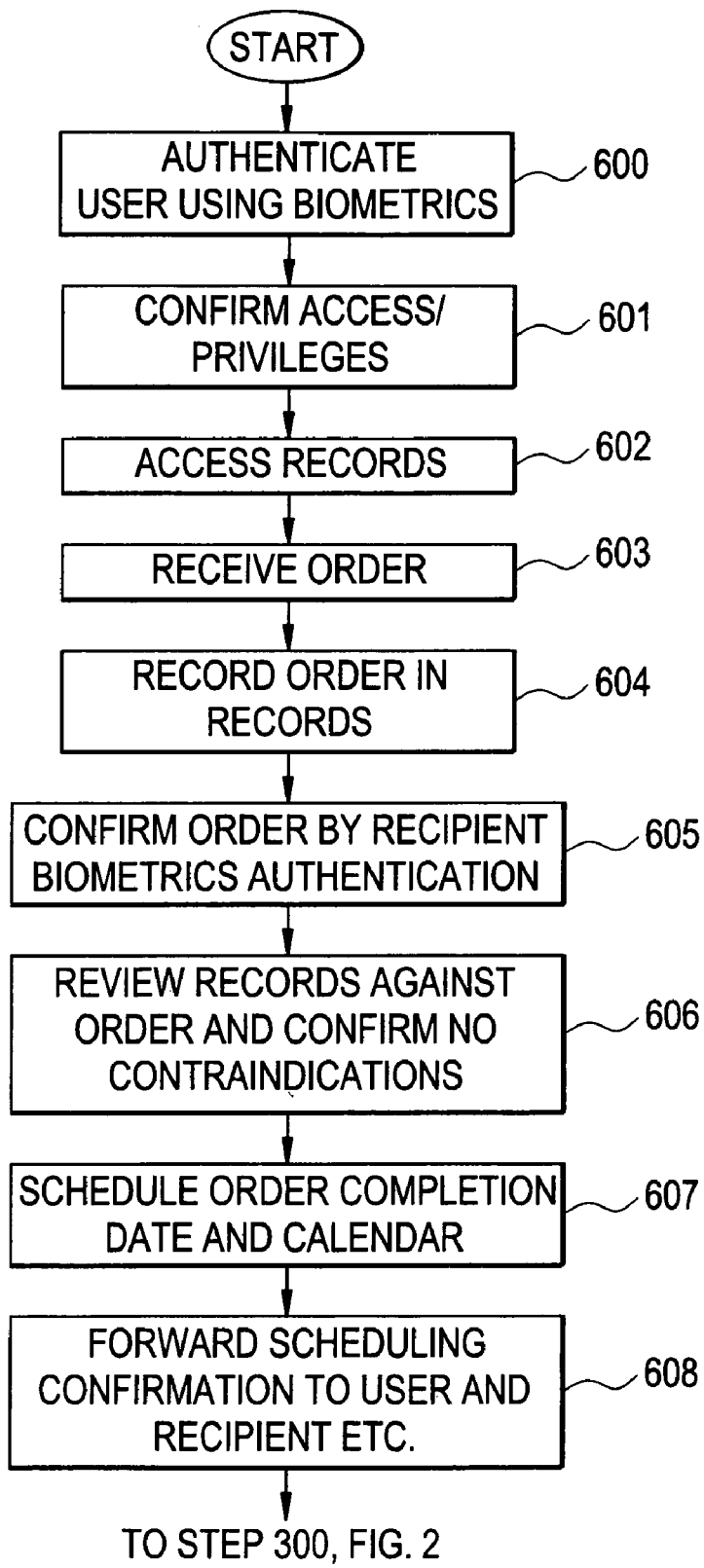

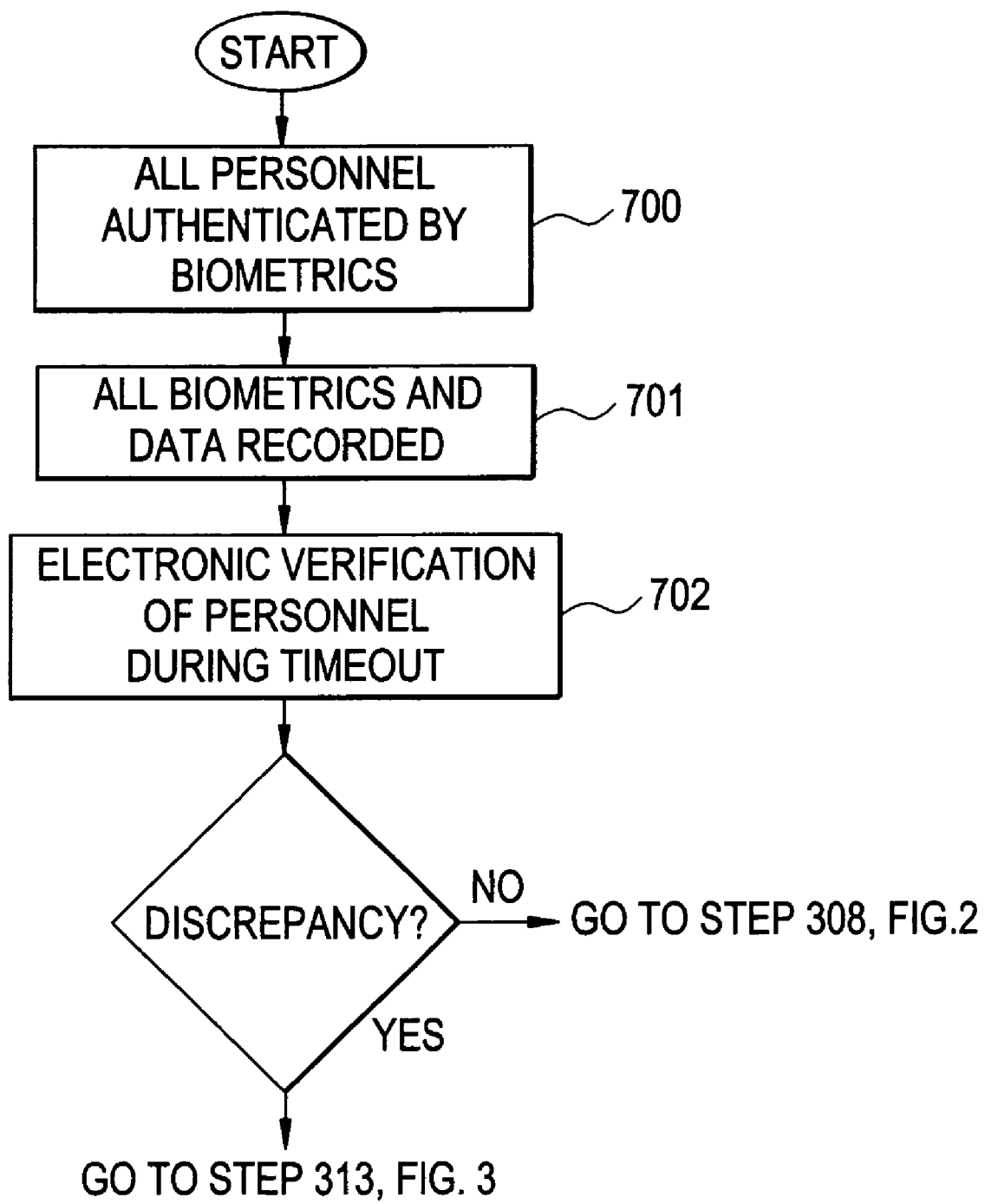

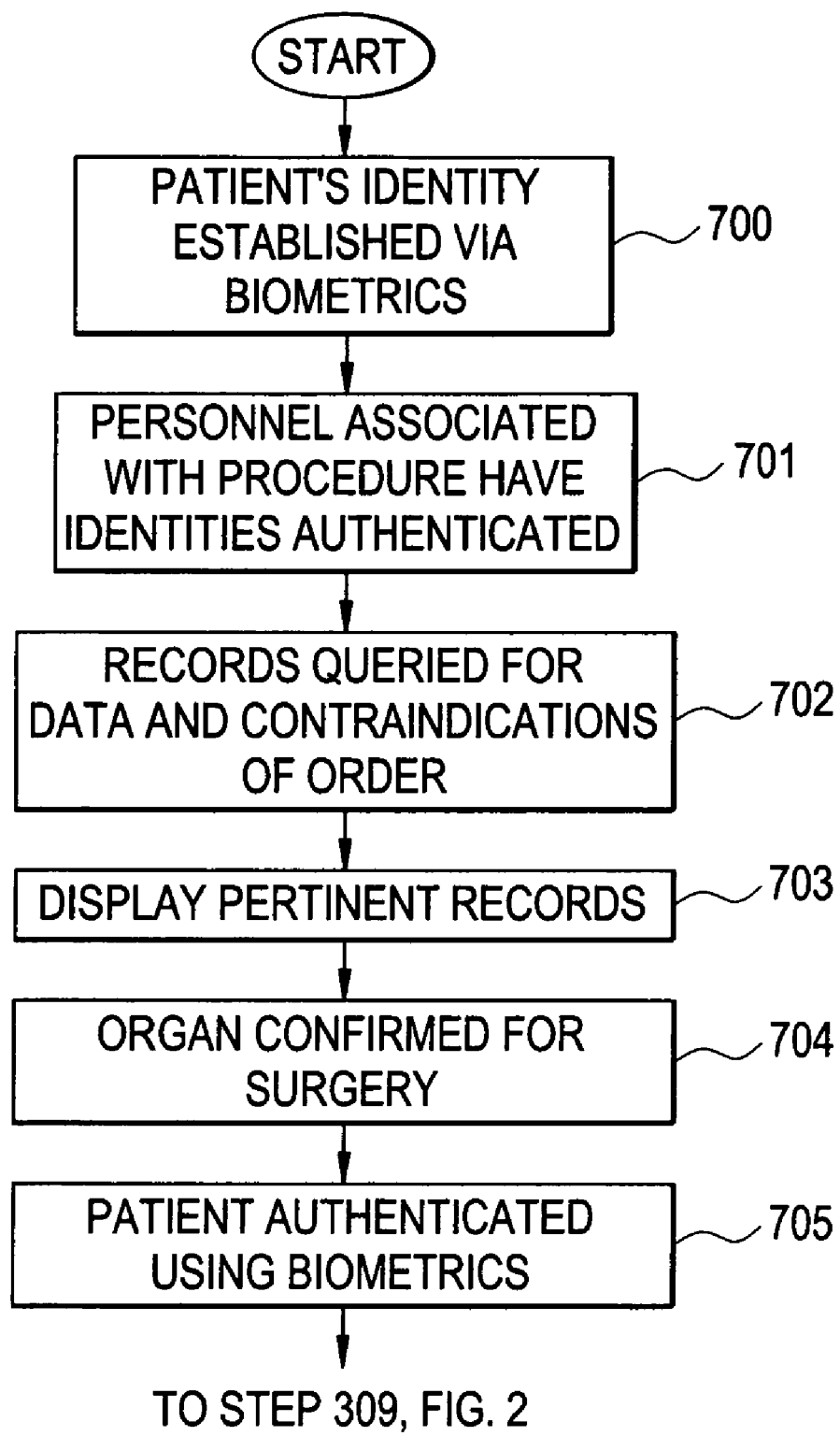

APPARATUS AND METHOD FOR UTILIZING BIOMETRICS IN MEDICAL APPLICATIONS

CROSS-REFERENCE TO RELATED APPLICATIONS

The present application claims benefit of priority from U.S. Provisional Application No. 60/795,199, filed Apr. 27, 2006, the contents of which are herein incorporated by reference in its entirety.

BACKGROUND OF THE INVENTION

1. Field of the Invention

The present invention relates to an access system which utilizes biometrics technology, to allow access to persons, equipment or facilities, and in particular, which uses biometrics in medical applications to prevent patient medical procedure errors, and to prevent fraud.

2. Description of the Related Art

The high frequency of medical errors and the adverse effect these errors have on clinical outcomes, has been of increasing concern. With new HIPAA and JCHAO regulations, healthcare institutions and practitioners are tasked with prioritizing patient safety, security, confidentiality, and reliability of data. In spite of these continuing efforts, patient identification errors remain an ongoing problem throughout the healthcare enterprise, including the medical imaging department.

Present patient identification systems utilize sub-optimal low technology patient identification methods such as wrist bands and verbal confirmation. These identification methods are prone to human error and may result in the performance of inappropriate tests and procedures, which can cause unnecessary morbidity, expense, radiation exposure, and even death.

Further, identity theft—including medical identity theft—has nearly tripled in the last four years, to more than 250,000 in 2005. Still further, misappropriation of medical records is on the rise—where erroneous entries could cause fatal consequences.

New biometrics technologies are currently available that obviate the potential for human error in misidentification by utilizing an anatomic feature unique to each patient. These include a number of different biometrics technologies such as facial recognition, fingerprint analysis, and retinal scanning, etc. Additionally, radiofrequency identification (RFID) technology exists, which allows for the tracking and auditing of an individual person or object as they matriculate throughout the enterprise. These technologies, in isolation or combination, provide the ability for authentication, identification, and surveillance of healthcare consumers (i.e., patients), as well as the healthcare providers (e.g., technologists, physicians, etc.).

However, none of these technologies has been integrated with medical applications to allow access to medical personnel, equipment and records, particularly over a variety of databases, whether local, regional, or national. Accordingly, the use of better patient identification technologies, such as biometrics, in medical applications, with access to patient records whether locally, regionally, and nationally, would be highly desirable.

SUMMARY OF THE INVENTION

The present invention relates to an access system which utilizes biometrics technology, to allow access to persons, equipment or facilities, and in particular, which uses biometrics in medical applications to provide access to equipment and records by medical personnel, and which prevents patient medical and surgical errors, and also which prevents fraud or access by unauthorized persons.

Accurate and rapid physiologic identification of patients in healthcare has a number of advantages that go beyond identification alone. The ability to create a unique patient-specific biometric patient identifier allows for the cross-referencing of medical information from disparate data sets and medical records. The digital capture of this information allows for instantaneous and reliable access of medical data across an electronic network that transcends geographic and temporal boundaries. In addition, this data can lead to improved utilization of medical services, improved diagnosis, and more timely treatment.

In one embodiment, a method of identifying and authenticating an individual for access or privileges, includes utilizing a biometrics device to obtain biometrics information on the individual; recording the biometric information on the individual in memory of an enterprise system of an enterprise; sending the biometrics information to one of a local, regional, or national database for identification; forwarding records on the individual from one of said local, regional or national database, when matched with the biometrics information, to a display of the enterprise system; and allowing access to at least one of the records, or the enterprise system, when the individual is matched for identity and authenticated.

If the individual is not matched with the database, an error message is displayed and registration of the biometrics and demographic information of the individual is requested and forwarded to one of a local, regional, and national database. The information in the database is cross-checked with the biometrics information, for accuracy, and editing may be performed if the information is not correct, at any point.

In one embodiment, the system displays an error message when records are not found regarding the procedure to be performed on the individual; and controls on the acquisition device are suspended accordingly. Before suspension is lifted, the individual's identification must be confirmed. A quality assurance audit of the suspension may be carried out.

In one embodiment, information regarding the scheduling of a predetermined procedure for the individual, and information on the scheduling of the procedure is forwarded to the individual and to the scheduler.

In one embodiment, registration and authentication of the individual is performed only at predetermined locations.

In one embodiment, the biometrics information includes at least two biometric scans on the individual.

In another embodiment, a secondary biometrics analysis of the individual is performed, and in one embodiment, performed at the acquisition device. In one embodiment, a third biometrics analysis is performed of the individual after editing of the individual's records takes place.

In one embodiment, a quality assurance audit is performed of the edited information.

In one embodiment, after the procedure is performed on the individual, the system delivers information from the procedure to a predetermined list of recipients, which list may be approved by the individual.

In one embodiment, a biometrics analysis is performed at the recipient to allow approved communication to take place between the individual and the recipient.

In one embodiment the individual may be a medical professional, who may issue an order and the order will be cross-referenced with the records to confirm that the privileges or access of the individual are commensurate with the order. In one embodiment, the order is confirmed by cross-referencing with a biometrics information of a recipient of the order, to ensure no contraindications are present.

If the individual lacks privileges, then a quality assurance audit will be initiated, and access to records, equipment, facilities, etc., will be denied to the individual. Further, fulfillment of the order will be denied when contraindications are present when cross-referenced regarding the order and the records, is performed.

In one embodiment, the biometrics input of the fulfillment department or individual authorized to fulfill the order is required for the order to be completed. Further, the order may be tagged upon fulfillment, and a biometrics input of the fulfillment individual completing the order, and of the recipient receiving the order, may be performed. A quality assurance audit may be initiated, and fulfillment of the order denied when the fulfillment department or individual is not authorized.

In one embodiment, a quality assurance audit may be initiated and the order denied to the recipient when biometrics analysis does not authenticate the recipient.

In one embodiment, the order is a prescription and the department or individual is a pharmacy or pharmacist. Further, the order may be a surgical procedure, and the department or individual may be a surgical center and the individual issuing the order may be a physician.

In one embodiment, the order completion date is scheduled and calendared, and forwarded to the individual and the recipient. In one embodiment, the individual is notified of scheduling and calendar items when the individual's biometrics is authenticated.

In one embodiment, a biometrics analysis of personnel at the surgical center and of the physician is performed to authenticate access and privileges to perform the surgical procedure. Further, a check of the databases is conducted to ensure there are no contraindications to performing the surgical procedure on the recipient.

In one embodiment, a timeout period is provided at the surgical center whereby electronic verification of the surgical procedure is confirmed by personnel at the surgical center and by the physician.

In one embodiment, the surgical site is confirmed on the recipient; and the recipient is authenticated for the surgical procedure using biometrics analysis.

In one embodiment, the biometrics information includes information on the individual's unique DNA genomic analysis, which is authenticated through records on the individual.

In one embodiment, the individual is a physician, and context-specific educational content is provided to the physician for review. The same may be performed for the patient.

In one embodiment, financial data related to the individual's financial accounts is provided when the individual's biometrics is authenticated.

In one embodiment, the order is checked against the databases to ensure controlled substances are correctly authorized.

In one embodiment, an apparatus which provides identification and authentication of an individual such that the individual can gain access or privileges or receive a procedure, at an enterprise, includes a device which allows access, provides a procedure, or acquires information on the individual, the device which is connected to or contains a database which stores the information; and a biometrics apparatus which obtains biometrics information on the individual, the biometrics information which is stored in the database; wherein the biometrics apparatus is integrated within the device; and wherein the biometrics information is cross-referenced with the database such that when information from the database on the individual matches the biometrics information, the device allows access to, allows a procedure on, or performs an acquisition on, the individual.

In one embodiment, a communication link forwards the biometrics information and the information stored in the database, to one of a local, regional, or national database.

In one embodiment, the device is an imaging device, pharmacy computer, physician computer, or surgical equipment.

In one embodiment, the biometrics information includes at least a fingerprint, palm print, voice recognition, facial recognition, retinal scan, venous flow identification, and electronic signature recognition.

In one embodiment, the enterprise is a school, prison, hospital, law enforcement facility, bank, or court.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 3 is a continuation flow chart of FIG. 2.

FIG. 4 is a flow chart of an access system with respect to placing medical orders, according to one embodiment consistent with the present invention.

FIG. 5 is a flow chart of an access system with respect to a physician's procedures in placing orders for a patient, according to one embodiment consistent with the present invention.

FIG. 6 is a flow chart of an access system at a surgical site, according to one embodiment consistent with the present invention.

FIG. 7 is a flow chart of an access system for confirming surgery on a patient, according to one embodiment consistent with the present invention.

DESCRIPTION OF THE INVENTION

The present invention relates to incorporating biometrics technology into medical or other applications, such that an individual's identification and authentication is assured in order to provide access to personnel, services, equipment, or facilities, prevent errors in medical treatment, and to prevent fraud. In particular, the present invention uses biometrics in medical applications to identify and authenticate patients, and medical professionals, to prevent patient medical or surgical procedure errors with respect to the patients.

Figure 1:
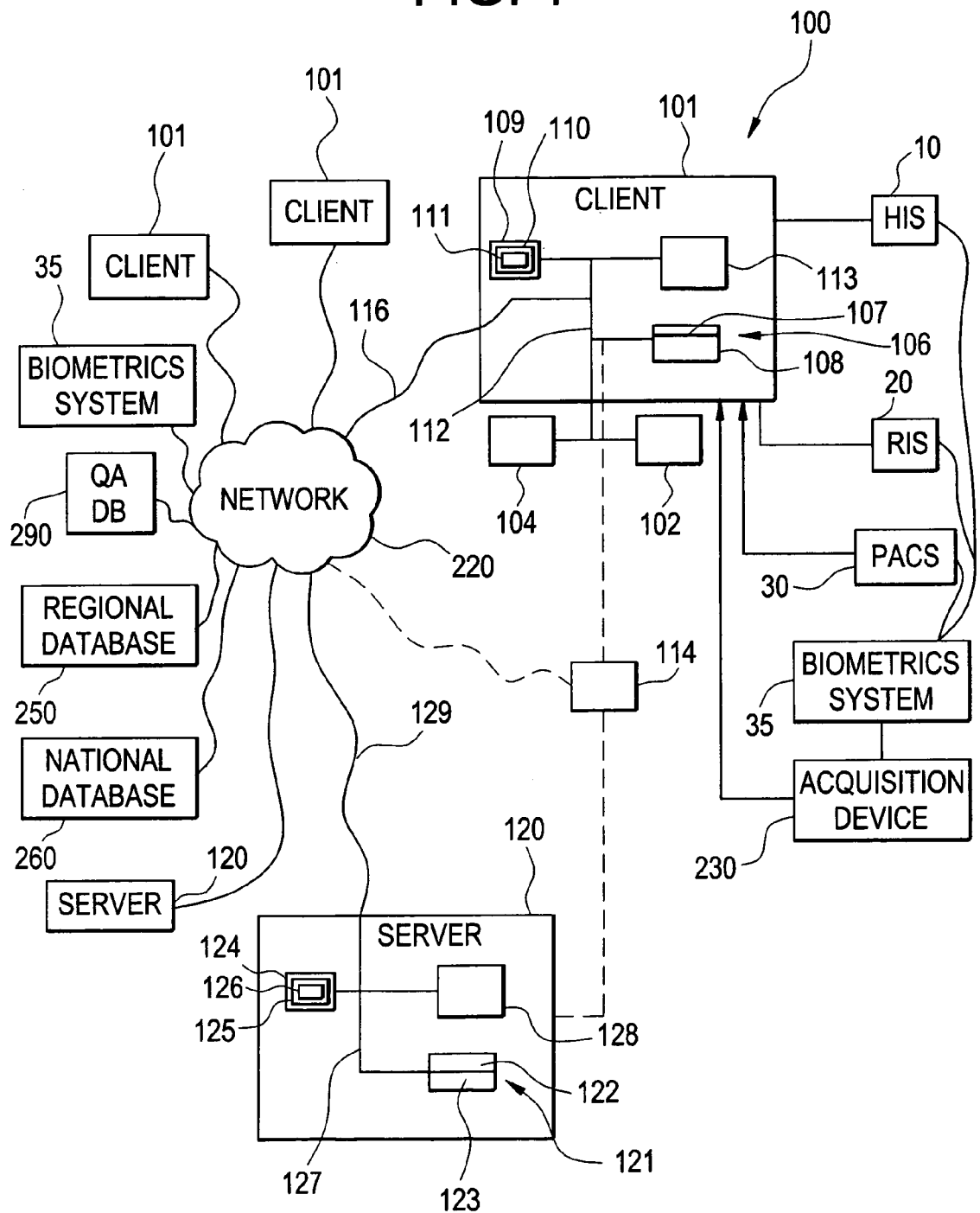
FIG. 1 is a schematic drawing of the major components of an access system according to one embodiment consistent with the present invention.

In the exemplary embodiment of a medical (in particular, radiological) application, the access system 100 of the present invention (see FIG. 1) is designed to interface with existing information systems such as a Hospital Information System (HIS) 10, a Radiology Information System (RIS) 20, a Picture Archiving and Communication System (PACS) 30, and to conform with the relevant standards, such as the Digital Imaging and Communications in Medicine (DICOM) standard, DICOM Structured Reporting (SR) standard, or the Radiological Society of North America's Integrating the Healthcare Enterprise (IHE) initiative.

The access system 100 of the present invention (see FIG. 1) includes a client computer 101, such as a PC, which may or not be interfaced or integrated with the PACS 30, and includes an imaging display device 102 capable of providing high resolution of digital images in 2-D or 3-D, for example. However, if the image resolution can be sufficiently high, the client may be a mobile terminal, such as a mobile computing device, or a mobile data organizer (PDA), operated by the user accessing the program remotely from the client.

Figure 2:
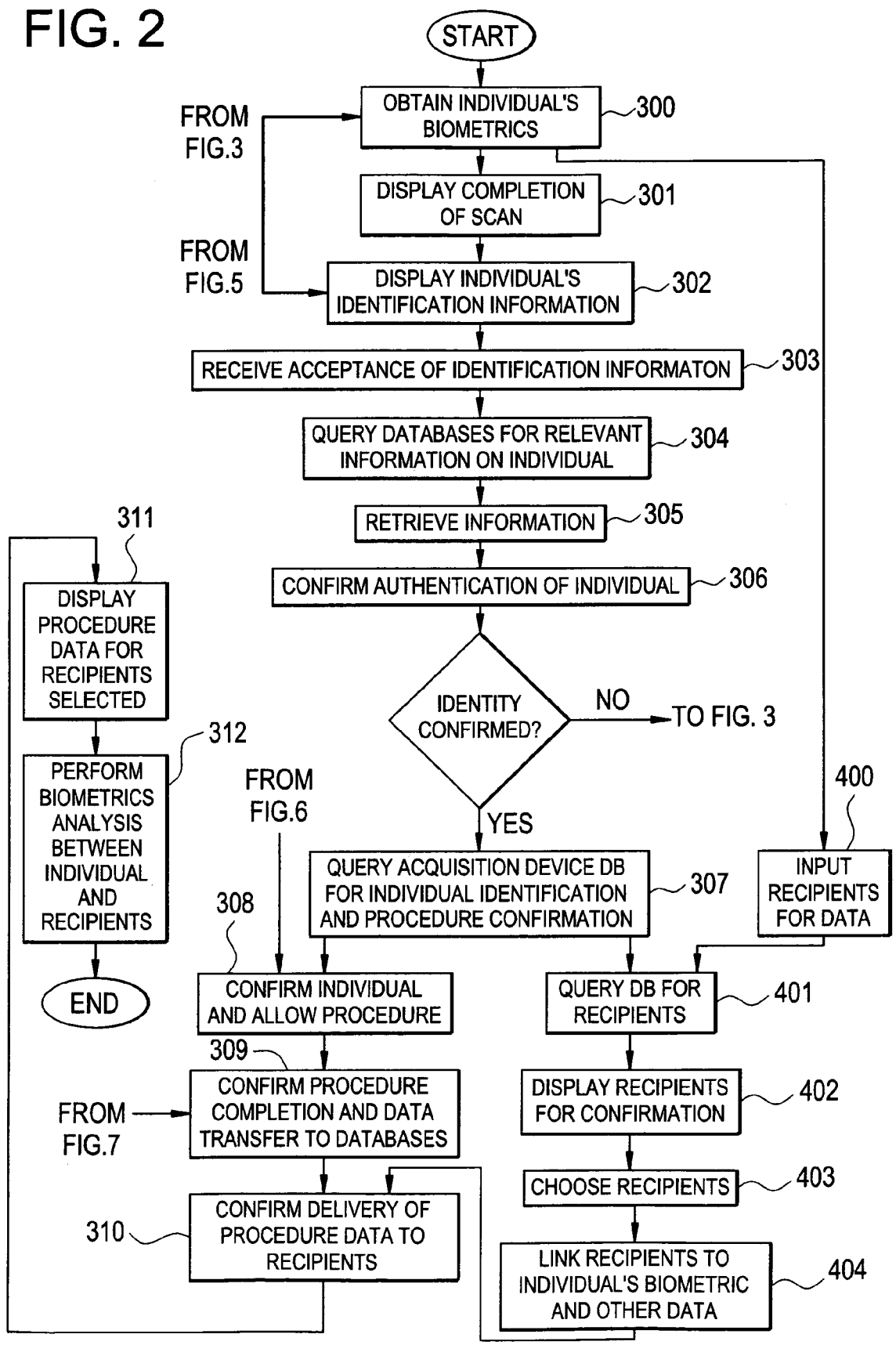
FIG. 2 is a flow chart of a biometrics method of access to an acquisition device according to one embodiment consistent with the present invention.

The biometrics technology of the present invention may include, among other things, biometric input means 35, such as a fingerprint scanner, a palm scanner, a microphone for voice recognition, a camera for face or retina recognition and photo identification, wrist scanner for venous flow identification, an electronic signature pad for electronic signature verification, etc., which is integrated with the client computer 101, and/or with imaging or other equipment 230 (see FIG. 2). The biometrics technology may be currently available or future-conceived. If the biometrics information is patient-inputted, instead of health care-professional inputted, the biometrics technology may be presented in a kiosk for privacy of the patient inputting the information.

Methods and systems consistent with the present invention are carried out by providing an input means 104 (see FIG. 1), or user selection means, including hot clickable icons etc., or selection buttons, in a menu, dialog box, or a roll-down window of an interface provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

The input means 104 is configured to accept the input from the biometric input means 35. Thus, bi-directional communication between the biometric input means 35 of the present invention, and the information systems, such as the HIS 10, RIS 20, and PACS 30, or equipment 230 such as a CT scanner, pharmacy dispensary, etc., allows the input means 35 to retrieve information from these systems and update information in the databases.

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 would include an input device or means 104, a display 102, and may also include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104 which would be used to draw the gestures or symbols of the present invention, directly onto the image displaying device 102.

In addition, high resolution goggles may be used to provide end users with the ability to review images without the physical constraints of an external computer. For example, a surgeon wearing specialized high resolution goggles to display the cross-sectional radiological image of a brain tumor in 3-D format, would be able to note the gestures on the image highlighting the pathology in question and reporting pertinent characteristics (i.e., anatomic localization, size, etc.), to serve as a guide during surgery. These goggles are used for image-guided surgery and gesture-based reporting would serve to provide consultation on pertinent findings during the course of surgery.

In another example, an internal medicine physician could use these specialized goggles outside the hospital, to review images with embedded gestures or symbols. The images could be downloaded using wireless technology and displayed on the goggles, thereby eliminating the need for a computer screen for image display.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system of the present invention is described as performing a certain function. However, one of ordinary skill in the art would know that the program 10 is what is performing the function rather than the entity of the system itself.

The program 110 which runs the access system of the present invention can include a separate program code for performing a desired operation, or may be a plurality of modules performing sub-operations of an operation, or may be part of a single module of a larger program 110 providing the operation.

The processor 106 may be adapted to access and/or execute a plurality of programs 10 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of biometric data, gesture symbols, or image files, for example.

The storage device 113 stores at least one data file, such as biometric data files, image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN. An internal storage device 113, or an external storage device 114 is optional, and data may also be received via a network and directly processed.

In methods and system consistent with the present invention, the client 101 may be connected to other clients 101 or servers 120, including administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program instructions. The communication link 116 may be at least partially included in the processor 106 executing corresponding program instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist of external connections, if the server 120 is constituted by a distributed system. The server processor 121 may have access to a storage device 128 for storing preferably large numbers of programs for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 220 such as a Local Area Network (LAN), Wide Area Network (WAN), and/or the Internet, over a communication link 1116, 129. Further, even though the systems HIS 10 and RIS 20, and PACS 30 (if separate) are shown as directly connected to the client 101, it is known that these systems could be connected to the client over a LAN, WAN, and/or the Internet via communication links. Further, in one embodiment, the biometrics input means 35 may be connected to the client 101, and to the LAN, WAN, or directly to the HIS 10, RIS 20, and PACS 30 etc., and/or to the imaging equipment 230 or other device or integrated therewith. Further, the biometrics input means 35 may additionally be connected to an external client at a physician's office, for example.

Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 and the biometrics input means 35 may include communications via a wireless service connection. The server system 120 may include communications with network/security features, via a wireless server, which connects to, for example, voice recognition. However, one of ordinary skill in the art would know that other systems may be included.

In another embodiment consistent with the present invention, the client system may be a basic system, and the server may include all of the components necessary to support the software platform of the present invention. Further, the present client-server system may be arranged such that the client system and/or the biometrics input means can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the present invention, may contain additional or different components.

Accordingly, in one embodiment consistent with the present invention, the access system 100 and method as used in an exemplary radiology access method and system, includes a client computer 101 with image displaying device 102, a biometrics input means 35, and an input device 104 which is a programmable stylus, for example, connected to the computer 101 and biometric input means 35.

The following are exemplary situations of how the present invention of incorporating biometrics technology into medical applications may be used to improve medical care within, for example, a medical imaging department:

In a first exemplary situation, a 60 year old female presents to an outpatient imaging center for a screening mammogram. She is uncertain of her past medical history but thinks she may have had a prior mammogram several years earlier, but is unsure of the exact date and location. In the current climate, the mammogram would be performed and interpreted by the radiologist without a comparison study. The radiologist identifies a subtle area of "indeterminate" microcalcifications and recommends biopsy to exclude underlying breast carcinoma. The biopsy is done at significant expense to the patient and pathology results indicate a benign etiology.

With the advent of biometrics, the patient's "signature" analysis is entered into a nationwide database which allows for previous patient specific medical information to be electronically accessed. This would provide the radiologist with all prior historical imaging studies and reports. By directly comparing the previous mammographic images performed five years earlier, the radiologist can reliably state that the "indeterminate" calcifications have remained stable and therefore can be assumed to be benign, and not require additional imaging or interventional procedures.

In a second exemplary situation, another patient presents to the emergency room after being found to be unconscious in a public restroom. The emergency medical personnel established a functional airway and documented adequate blood pressure and pulse. Because no family member is present, no past medical history can be obtained. The emergency room physician orders an emergent CT of the brain with and without intravenous contrast to evaluate for intracranial pathology. The patient is transported to the radiology department after intravenous access is established. Shortly after injection of the intravenous contrast, the patient experiences an anaphylactic reaction, and goes into shock.

Using biometrics, the patient's identification could have been instantaneously established and past medical records retrieved prior to the order for the CT scan. These records would have documented past allergic reaction to intravenous contrast as well as a longstanding history of seizures and non-compliance to prescribed therapy. With this additional information, the emergency room physician could order a blood test to determine whether the patient is taking the prescribed anti-seizure medication and change the imaging order to an MRI. This would avoid administration of iodinated contrast and provide more detailed information relevant to the underlying seizure disorder.

In a third exemplary situation, a patient (i.e., "Eliot Siegel") presents for an elective screening ultrasound to evaluate an abdominal aortic aneurysm (AAA). During the registration process, the clerk misspells the patient's name (i.e., "Elliot Seigel") and the technologist enters this incorrectly spelled name into the RIS/PACS. The computer program searches its database and retrieves another patient's imaging file (i.e., "Elliot Siegel"), which had an abdominal ultrasound done 6 months ago which was normal. When the radiologist compares the current study with the historical comparison (of the wrong patient), he/she incorrectly diagnoses the AAA as a new finding, requiring emergent surgical consultation.

However, using biometrics, the data entry error would have been eliminated and the correct medical imaging folder accessed. This would show that "Eliot Siegel" has had annual ultrasound exams demonstrating a stable 3.5 cm AAA, which has remained unchanged for 4 years. As a result, no further evaluation is required.

Accordingly, the present invention would be helpful in all the above exemplary situations, to avoid problems which could arise in the identification of patients or location or immediate availability of their medical history.

Thus, the present invention relates to a biometrics technology 35 (e.g., facial recognition technology, fingerprint analysis, etc.) which is used to identify and authenticate a patient—for example, prior to a medical procedure or test, and in one embodiment, is directly integrated into a medical device (i.e., medical imaging acquisition technology 230, such as a CT scanner) for medical procedure error-proofing.

Specifically, the biometrics technology includes a biometric input means 35 and is connected to the operating system 100 of the medical enterprise or integrated with a component, such as a physician or hospital's computer terminal 101, 30 or acquisition device 230. All information inputted into the biometrics system 35 is recorded in at memory or a database 109, 113 etc., which can be accessed by the program 110 such that pertinent information can be retrieved, sorted, and analyzed.

The biometrics technology provides the means 35 for both authentication (e.g., patient claiming to be "Charles Smith") and identification (e.g., unknown patient presents for examination, "who is he?") of the presenting individual. Once the biometrics device 35 scans the individual in question, the unique identification data is simultaneously sent by the program 110 to local 128 (or 113, 114), regional 250, and national databases 260 for bidirectional data access and transfer. Using artificial intelligence (e.g., neural networks), all relevant medical data as predefined by the program 110, and is transferred automatically from the identified patient's database 113, 114 to the local database 114, 128 to assist with exam selection, protocol, and analysis.

In particular, the present invention is directed to user and patient authentication/identification which is required for all events that occur in the patient care continuum including (but not limited to): all medical imaging studies (e.g., MRI, ultrasound); imaging studies outside of radiology (e.g. colonoscopy, ophthalmology); all medical procedures (e.g. biopsy, surgery); all patient encounters (e.g. clinic visit, ER admission); and all forms of medical treatment (e.g. drug delivery, blood transfusion). Further, all physician-patient communications (e.g. consultations, notification of test results), would be considered part of the scope of the present invention.

There are several exemplary embodiments in which the present invention can be applied within the medical enterprise.

In one embodiment consistent with the present invention, the patient presents for a scheduled diagnostic imaging exam (e.g. CT).

Specifically, a patient is seen in a physician's office and a CT exam is requested by the physician for a specific diagnosis (i.e., abdominal pain, rule our aortic aneurysm). When the order is electronically scheduled, the patient undergoes biometrics analysis (using a portable biometrics device 35 integrated into the physician's computer 270), by a physician's assistant.

When the information is scanned into the biometrics device 35, it is recorded in memory into a database of patient information 109, 113, 114, 128 etc. The program 110 then scans the database 109, 113, 114 etc. for matching information. If the patient's identification is matched in the database 109, 113 etc., the information is presented on the display of the biometrics device 35, or the display means 102, along with the relevant patient information, (i.e., name, date of birth, address, social security number, relevant medical history, allergies, doctor's name, insurance information, etc.). Thus, the day, time, and location of the scheduled CT exam is inputted into the patient's medical records, and the patient is provided with the information by the program 110.

If the patient biometrics information is not matched in the database 109, 113 etc., then the program 110 will display for the user, information that the patient is not recognized. The program 110 will then provide a login display, so that the user can formally register the patient. The login information will include the biometrics information, and demographic information such as patient name, address, date of birth, social security number, relevant medical history, doctor's name, insurance information, etc. In one embodiment, registration of a new patient can be performed only at pre-determined locations within the medical enterprise (i.e., doctor's office, hospital, out-patient facility etc.).

In the initial biometrics input, a detailed biometrics analysis is performed by the program 110, consisting of at least one, and preferably two different biometrics analyses for the purposes of redundancy. For example, fingerprinting and a retinal scan, or fingerprinting and a photograph for the use of facial recognition technology, etc. Despite the amount of information required, the registration process should be routine and take no more than approximately 30 minutes for completion.

Once inputted, this biometrics "electronic signature" (i.e., combined biometrics/demographic registration data) is stored by the program 110 in a standardized XML format in an electronic database 109, 113, 114 etc. so that all patients can be tracked as they matriculate to different medical institutions. The biometrics data associated with this "signature" is also stored by the program 110 in the DICOM structured report information, in a separate XML format. This provides for redundancy of the data in the event that one archive is nonfunctional at any single point in time.

In addition, the program 110 automatically and simultaneously transfers all the data to local 128, regional 250, and national databases 260 on the network. The transfer of the biometrics data is independent of the vendor and individual biometrics device 35 used. For security, the local acquisition data and stored network data are then cross-referenced for accuracy by the program 110, and a correct match is determined. This feedback can be provided as a binary function (i.e., yes or no) or as a probability statistic (e.g. 1 in 100,000,000), or in any other manner which would provide a measurable assurance of accuracy. The feedback is provided by the program 110 at the local acquisition level.

The biometrics/demographic data becomes an integral part of the patient's electronic medical record (EMR), which is available to the patient and his doctors, and other medical personnel at any location which subscribes to the database 113 etc.

Once the registration process is completed, or the patient is identified using the biometrics program 110, the previously requested CT exam is electronically scheduled and stored in the database 113, 114, 128 etc. In addition, the program 110 automatically sends electronic notifications (i.e., e-mail, facsimile etc.) to the patient and the ordering physician.

When the patient arrives for the scheduled CT exam, at the predetermined location (i.e., a medical imaging department of a hospital, etc.), the patient will undergo biometrics analysis at a registration terminal 101.

Upon the biometrics data being inputted using the biometrics device 35, the program 110 will search the database 113, 114, 128 etc. to determine whether the identification-specific data is recognized within the database.

If it is, the program 110 will prompt the user or patient to confirm their name, ordering physician, exam type, day/time of the scheduled exam, etc. Note that the registration terminals 101 may be set up for use by a patient or by a health care professional, when the patient arrives for the examination. The registration terminal 101 may be a kiosk for patient privacy. However, for security reasons, the biometrics and demographic information is inputted only by a health care or other professional affiliated with the medical enterprise.

If the information displayed by the program 110 is confirmed by the patient, and no edits are required, the patient logs into the system 100 and instructions are displayed by the program 110 which inform the user to travel to the CT waiting area. In one embodiment, directions and/or maps may be printed out at the terminal 101 for the patient's information.

If the information provided is incorrect when the program 110 cross-references the information to the database 1113, 114, 250 etc., then the program 110 will query the patient to input any required modifications. Any editing to the data automatically triggers the program 110 to perform an electronic QA auditing trail. The program 110 will incorporate the modified data into the EMR once the modified information is verified by the patient.

The patient will undergo biometrics authentication one more time at the acquisition device (i.e., CT scanner) 230. The time required to verify the patient identification would be minimal (i.e., on the order of 15 seconds), but would prevent medical errors and fraud.

In one embodiment, and preferably, the biometric device 35 can be directly installed into the imaging modality (e.g., CT or CR unit 230), so that the technologist can perform the identification "on the spot".

In an exemplary operation, the following steps include the sequence which the imaging technologist would follow in using the biometrics technology for patient identification, data access, and image review.

For example, in step 300 (see FIG. 2) the technologist may hold the patient's wrist in front of the scanning device in order to obtain a patient-specific signature blood flow (in the case of a vascular wrist scanning device as a biometrics signature, for example). Analogous actions would be taken for a fingerprint device, retinal scanner, or other biometric patient identification system. Thus, the biometrics scan would be performed and the data recorded in the system 100.

Once the biometrics scan is completed, in step 301, the program 110 would display a message on the console of the scanner, for example, indicating completion. A feedback cue such as a green light or a tone may be used to indicate that a successful match has been made with the local and national databases 128, 250, 260. The program 110 may then provide an electronic read-out of the patient name, age, imaging exam ordered, clinical indication, and ordering physician for verification by the technologist, in step 302.

In step 303, the technologist may accept the identification by clicking on the "Accept" icon displayed by the program 110 on the computer screen 102. This elicits an electronic query by the program 110, in step 304, of the local, regional, and national electronic databases 128, 250, 260 for relevant electronic medical and imaging data to be automatically retrieved and sent to the local EMR and PACS for interpretation and review if it has not been retrieved already. An alternative action would be to merely index the type of information and location and not require that it to be actually transferred.

By utilizing this approach at the local level, utilization of imaging services can be improved (by eliminating redundant exams), adverse reactions can be substantially reduced (by direct access to the EMR and past medical history), and diagnosis can be improved (by providing all relevant historical imaging and clinical data). This same technology can be applied throughout the medical enterprise to improve patient identification for blood transfusions, administration of drugs, and surgical procedures.

Once the patient's identification has been established using the biometrics technology at the acquisition device 35, an electronic message is sent by the program 110 in step 305 to both the on-site EMR and PACS (to retrieve all relevant medical and imaging data), as well as to regional and national archives 128, 250, 260 as stated previously.

Once authentication is completed and confirmed in step 306, the acquisition device's (CT) database is electronically queried by the program 110 using Modality Worklist software, to identify the patient and exam in the database 113, 114, 250, etc. If the patient and exam data match the acquisition device database 113, as determined by the program in step 307, the technologist confirms receipt and prepares the patient for the exam to begin in step 308.

In one embodiment, both biometrics and acquisition device authentication can be performed in the same step.

All data acquired during the exam performance is entered and stored in the database 113 and simultaneously sent to the following databases: patient EMR, acquisition device (CT) database, PACS 30, hospital database 128 etc., regional database 250, and a centralized secure national database 260. Accordingly, all the patient data is available to all health care professionals simultaneously and all data is current.

In one embodiment, the biometrics authentication data (in XML schema), is incorporated into the DICOM header by the program 110, which is attached to each imaging data set. This biometrics "tag" accompanies the imaging data as it is transferred to each database 113, 114, 128, 250, 260 etc. (along with the patient's EMR) by the program 110.

The data contained within the DICOM header includes: 1) type of exam; 2) location of acquisition; 3) specific scanning device; 4) date and time of exam acquisition (start and completion times); 5) technologist identification; and 6) specific mode of biometrics authentication, among other relevant information.

Once the medical imaging exam has been completed, the technologist is prompted by the program 110 (at the acquisition device 230) in step 309 to confirm the exam completion and data transfer to the various databases 113, 114, 128, 250, 260 etc. (i.e., patient EMR, PACS 30, local database 240 and regional database 250, and secure national database 260). In one embodiment, the patient is separately prompted by the program 110 (at the acquisition device 230) to approve automatic delivery of imaging data to the list of physicians tied to the patient-specific biometric signature, in step 310.

Any subsequent communication (relative to that imaging data) between the patient and physician (e.g., consultation, recommendation for additional imaging, biopsy, etc.) can be automatically entered into the patient's records by the program 110, and any subsequent or follow-up exam may be initiated by the patient once again undergoing identification and authentication at a biometrics device 35 for the additional testing.

Once patient identification has successfully occurred, the patient will be presented in step 311 by the program 110 with recent data entered into their EMR (including their scan results). Upon review of their records, the program 110 will present the patient with a list of physicians in step 312 such that the patient may select the physician desired, and direct an electronic query to that physician regarding their test results or any topic in step 313.

Subsequent electronic communication between patient and physician can be initiated by the program 110 only after successful biometrics identification and/or authentication of both parties (thereby providing additional functionality to the biometrics signature).

If patient authentication fails at the acquisition device 230—for example, the patient is not recognized (e.g., new patient or distorted biometric signature)—then the technologist is sent an alert or error message by the program 110 in step 313 (see FIG. 3), which is displayed on the screen 102, requesting additional validation, and the program 110 prevents the acquisition device 230 (and technologist) from proceeding to the data acquisition phase by suspending controls on the acquisition device 230 in step 314.

In that event, patient identification now needs to be established in step 315 before proceeding further. This can be performed by designated personnel (e.g., technologist, physician), who have administrative controls over the acquisition device 230, in one of three ways—by: 1) including demographic data intrinsic to the patient (i.e., showing of identification data by the patient to confirm identity) (step 316); 2) using an alternative biometrics device 35 (i.e., fingerprint matching instead of facial recognition, for example) (step 317); or 3) performing re-registration of the patient into the databases 113, 240-260 (step 318).

In the second option, if no match is found, then the patient is assumed to be new to the system 110 and this is confirmed by manually querying the system 100 with patient identifying data (name, social security number, etc.) (step 319).

Before entering the patient as a "new" patient, the biometrics signatures are automatically sent to regional 250 and national archives 260 for comparison by the program 110 (see step 304). If a match is made, then the previous patient data is retrieved and copied by the program 110 into the current archive 113, for example, if the other information is consistent in identifying the patient. If no match is made, the patient is entered as a "new" patient simultaneously within the local, regional, and national biometrics archives 240-260, by the program 110 (see step 300).

Whenever a failure in authentication occurs, or editing of the patient information is required, the program 110, in step 321, initiates an automatic QA audit trail and all data inputted into the databases 113, 250, 260 etc. is recorded in a separate QA database 290 by the program 110 in step 322 (along with the identification of the person inputting the data), for review, analysis, and security verification. In one embodiment, separate alert messages of the authentication/identification failure or modification, are automatically sent to the patient's EMR and centralized security database 250, 260 by the program in step 323 for future tracking and analysis.

Once authentication is substantiated after an identification/authentication failure, the program 110 will remove the lock on the controls of the acquisition device 230, and the technologist will then be able to proceed with image acquisition as in step 308.

Although the above scenario involves a scheduled examination, alternative scenarios could be envisioned.

In another embodiment consistent with the present invention, the patient presents to an imaging department for a screening exam (e.g., mammography) without pre-authorization or scheduling.

The steps involved in the unscheduled visit would be similar as to the scheduled visit. At the initial check-in procedure, the patient's desired screening (i.e., non-diagnostic) examination (e.g., mammography, vascular ultrasound) is inputted into the database 113, 114 etc. by the program 110 in step 400 (see FIG. 4). The program 110 will query the patient identification database 113, for example (contained within the EMR) to identify names of physicians involved in that specific patient's care in step 401. The program 110 will then display a list of corresponding physicians linked to the patient's EMR and ask the patient to confirm or deny sharing of any imaging data or test results with those physicians in step 402.

In one embodiment, at least the patient's primary care physician must receive the results of the imaging data or test results. However, in another embodiment, the patient may select the physicians from a list displayed by the program 110, to whom the patient wants that specific exam data electronically sent. If additional physician names are desired by the patient, the additional physicians can be inputted into the system 100 by name, address, etc., and recorded by the program 110. The program 110 will add the physician to the EMR queue and link the patient's biometrics data (specific to that patient), to the physician, in step 405. The program 110 will then display these additional physicians for the patient, and the patient may choose the physician for receipt of the data or test results, in step 310 (see FIG. 2).

Thus, all data acquired by the exam performance is simultaneously sent to the various databases 113, 114, 250, 260 etc., by the program 110, as well as electronically forwarded to the selected physicians in step 310.

In another embodiment consistent with the present invention, the physician is required to prescribe medical treatment (e.g., drug delivery or blood transfusion) on a patient at a medical enterprise.

In this scenario, the physician must first be authenticated by the biometrics technology 35 at the medical enterprise in step 500 (see FIG. 3). Once identification/authentication is completed, the physician enters the desired order (e.g., drug prescription) into the patient's EMR in step 501. Based on the physician's biometrics signature, the program 110 will cross-reference the physician's privileges with the entered order in step 502, to ensure that the prescribing physician is authorized to prescribe care for the patient, and has the privileges to order the prescribed medicine or the prospective treatment.

If the program 110 determines that the order matches the physician's privileges in step 504, then the program 110 will provide an electronic confirmation of the order to the physician in step 505.

In addition, the program 110 will ascertain, in step 506, the lack of medical contraindication (e.g., medical allergy) for the patient of fulfilling the drug order, and also ascertain from the EMR that the drug order is appropriate in view of the patient's medical history.

If the program 110 determines that the order is appropriate in step 507, the order will be transferred an entered into the hospital database 128, 113, 114 etc. in step 508. Further, a copy of the order is automatically sent from the hospital database 240 by the program 110, in step 509, to the pharmacy information system if it is a prescription, or to the department handling the procedure (i.e., in the case of blood work etc.).

The program 110 will automatically notify the pharmacist/pharmacy of the incoming drug order in step 510, and the pharmacist will be required to input his biometrics information in order to fulfill the prescription in step 511. The program 110 will receive the biometrics information and perform a biometrics analysis (i.e., user identification/authentication) on the data received in step 512, and all data (i.e., name of pharmacist, date/time order filled, medication name and dosage, patient name and location) related to that specific drug order is recorded in the multiple databases using standardized XML schema using the program 110 in step 513.

Once the pharmacist fills the prescription, the medication is tagged with RFID and is sent to the nursing station (if in a hospital environment) for drug delivery to the patient in step 514. The nurse receiving and dispensing medication must enter their biometrics information in step 515 into the biometrics input means 35, in order to be identified and authenticated.

Once the nurse is identified and authenticated by the program 110 in step 516, and their privileges for drug dispensary are approved by the program 110, the program 110 will record the data into the databases 113, 114 etc. in step 517 (i.e., name of nurse, drug name and dosage, date/time drug received, patient name and location).

Further, prior to the drug being dispensed to the patient, the patient must be identified and authenticated by the program 110—using a portable biometrics device 35, for example, in step 518.

Further, the program 110 records the administration of the drug to the prescribed patient by medication RFID (for drug authentication and tracking) in step 519. If multiple medications are to be dispensed to the particular patient, then each individual drug is entered into the appropriate databases 113 etc. by the program 110 along with the patient's biometrics data.

The program 110 will electronically send notification of the drug delivery to the ordering physician in step 520 with receipt confirmation by the physician required by the program 110 (to include the physician's biometrics signature).

If the physician's (or pharmacist's, nurse's, or patient's) authentication fails in steps 504, 507, 516, a QA audit trail is initiated by the program 110 in step 521. The physician may re-attempt authentication by an alternative method as described previously (i.e., alternative biometrics device or physician-specific demographic data), in step 500.

If authentication is eventually approved by the program 110 in step 504 after alternative methods are used, then the physician may re-enter the order in step 501. If authentication continues to fail, then the program 110 will lock the physician out of the drug ordering system in step 522, and only an override of the program 110 in step 523 by an approved administrative or supervisory input will allow the drug order to take place.

If the order is rejected by the program 110 based on lack of approval of the biometrics with respect to the physician's privileges in step 504, then the physician has the option to either re-enter an alternative order in step 500/501 or discontinue the process. Note that an order rejection also triggers an automatic QA audit trail by the program in step 507, as described above.

As stated above, if the program 110 issues an "error" message at any time during the above sequence of events, due to lack of physician privileges, drug contraindications, etc., a QA audit trail is automatically initiated by the program 110 (which includes patient outcome analysis) in step 521.

In one embodiment, in order for drug delivery to proceed, a second authenticated party (e.g., charge nurse) may be required by the program 110 to confirm the order, drug, dosage, and the patient, are correct and appropriate.

In yet another embodiment consistent with the present invention, the patient may present to the medical enterprise for a therapeutic procedure (e.g., biopsy or surgery).

In this embodiment, the patient may present first for medical evaluation to their primary care physician. The primary care physician may then access medical data from the patient's EMR using the present program 110 in step 601 (see FIG. 5) by first undergoing electronic authentication (to verify their identity) in step 600 and to ensure that he/she has the necessary privileges for review of the patient's records. The physician's identity and medical privileges are determined through biometric analysis by the program 110 in step 601, which is inputted using an input means 104 at a secure, local biometrics device 35 integrated into the physician's office computer 101.

Once the physician's identity and privileges are authenticated by the program 110 in step 601, the patient's EMR which was accessed in step 602, is reviewed by the physician, and in this exemplary embodiment, it is determined by the physician that a previous diagnostic test (e.g., chest CT) has identified a nonspecific lung nodule, with the recommendation for a diagnostic lung biopsy, for example.

The primary care physician may then electronically place an order for thoracic surgery consultation and biopsy in step 603, for example, to the hospital database 113, 114 etc. and record the order in the patient's EMR using the program 110 in step 604.

In one embodiment consistent with the present invention, the patient may be asked to undergo biometric identification and authentication by the program 110 in step 605 to ensure that the order is confirmed for that patient, and that the biopsy is correctly scheduled.

Once the patient is authenticated by the program 110 in step 605, the appropriate medical data within the patient's EMR is reviewed by the program 110 in step 606 (using artificial intelligence such as neural networks), and the chest CT report and recommendation for biopsy is confirmed in step 609. This program 110 step ensures that there is nothing in the patient's medical history that would contraindicate any scheduled tests (for example, a CT scan for a patient with allergies to the imaging medication).

The program 110 would then schedule a surgical consultation and biopsy in step 607 after accessing the OR and surgeon's calendars, and the order would be electronically transmitted by the program 110 to the thoracic surgical specialist.

In addition, the program 110 will forward an electronic message to the patient and to the physician in step 608 notifying them of the confirmation of the order, and the scheduling information.

When the patient presents at the hospital for the procedure, the patient will need to register in step 300 (see FIG. 2) using the biometrics procedure as outlined previously. At the OR, the physician will undergo biometric analysis for authentication and access to the patient's EMR in step 614 where the consultation notes and informed consent forms are entered into the database 113, 114 etc.

Further, before the surgical preparation can begin, the patient again undergoes biometric identification and authentication in the OR suite in steps 300-307.

All personnel involved in the procedure (e.g., nurses, anesthesiologist, surgeon) must also undergo biometrics authentication before the procedure may begin, in step 700 (see FIG. 6). Further, all data (i.e., name, date, time, clinical indication procedure to be performed, anatomic location, etc.) are recorded in the EMR and biometrics databases by the program 110 in step 701, in addition to all the information on the personnel involved in the procedure, and who are authenticated by the program 110.

In order to ensure that the patient, procedure, and anatomic location are correct; an electronic "time out" is initiated, such that electronic verification is provided by all surgical staff involved in step 702, as a final check by the program 110.

If any discrepancy exists that precludes the procedure being safely performed (e.g., allergy to the prescribed anesthesia, incomplete authentication of personnel etc.), an error message will be displayed by the program 110 in step 703 that will necessitate immediate attention by the surgical personnel, lock down of any equipment which is controlled by the program 110 in step 314 (see FIG. 3), and require immediate termination and/or adjustment of the protocol by the surgeon and physician in steps 315-318.

Once any discrepancy is removed, or the data inputted is completed, accepted, and authenticated where necessary, in steps 315-318 by the QA, EMR, and biometrics databases 113, 114, 250, 260, etc. then the program 110 will display a message allowing the procedure to proceed in step 308.

As the procedure takes place, all clinical data intrinsic to the procedure is recorded into the databases 113, 114, etc. by the surgical personnel (e.g., anesthesia, vital signs, intraoperative photographs) in step 309 and directly integrated into the patient's EMR by the program 110.

After completion of the procedure, the surgical operative note (and associated data) is recorded with an electronic consultation, by the surgeon in step 311, in the system 100, and the program 110 will send the note and consultation to the primary care (referring) physician in electronic form.

Further, after the procedure, the biopsy specimen is marked with the patient's identifying information through RFID labeling and transported to Pathology for frozen section analysis, for example, in step 509 (see FIG. 4). When the pathologist receives the surgical specimen, and before beginning analysis, the pathologist must undergo biometrics authentication in step 511 by logging into the hospital database 113, 114, etc. for example. In addition, the receipt of the surgical specimen, and the RFID tag assigned thereto, is entered into the appropriate hospital/pathology databases 113, 114 etc. to verify consistency and authenticity of the data, in step 513.

The pathologist preliminary analysis is then recorded into the patient EMR, QA and biometrics databases 113, 114 etc., in step 513 and the program 110 will automatically forward the pathology results to the surgeon and the physician for review in step 520. However, as previously noted, the surgeon and physician—an in fact, any personnel authorized to view the pathology report or the patient's EMR—must be authenticated for identity and clinical privileges in step 518 before access is provided by the program 110.

The patient's recovery status is monitored in the recovery room where all relevant data is recorded into the EMR (after authentication of the nursing staff as noted above). Further, before being discharged (with pain medications in accordance with the program protocols described above), the patient undergoes repeat biometrics authentication along with RFID tagging and electronic receipt of the pharmaceuticals recorded in the system, in step 635, as shown in FIG. 4.

In yet another embodiment consistent with the present invention, educational programs can be linked directly to the physician or patient's biometrics signature. These physician educational programs can be customized to individual preferences, tied to continuing medical education (CME) requirements, or specific patient diagnoses.

For example, if a patient under a physician's care has just undergone surgical exploration for an abdominal mass and is found on pathology to have an unusual neoplasm (e.g. carcinoid tumor), the patient-specific medical data is automatically transferred by the program 110 to that physician's database 113 etc., based on his/her biometrics signature and provides him/her with educational information tied to that new diagnosis.

The same methodology can be applied to patient educational programs, based on their medical history, drug therapy, tests, procedures, etc. As new data is saved within the patient's medical database by the program 110, context-specific educational content is provided by the program 110 to the patient for optional review. The patient (or physician) would simply go to a biometrics device 35 for authentication/identification and once authentication is completed, the program 110 would query the databases 113, 114 etc. and new user-specific educational content would be provided based on new data elements contained within the biometrics-linked databases 113, 114 etc.

In another embodiment consistent with the present invention, the program 110 can provide biometrics-linked updates and reminders, where a patient can have electronic notification of medical appointments, diagnostic tests, treatment regimens, etc., delivered by the program 10 to their biometrics-linked database 113, 114 etc. Whenever the patient signs into a biometrics device 35 for authentication (or identification), these updates would be presented to the patient by the program 110 on a daily basis. The same type of application can be used by physicians regarding their daily work schedules, alerts to test results, or medical queries. Further, another type of biometrics-linked reminder can remind patient as to daily schedules for drug regimens.

In another embodiment consistent with the present invention, biometrics-linked business/financial data can be provided to a user. In a manner similar to accessing data from the EMR, other information systems within the medical enterprise can be integrated into a comprehensive database 113, 114 etc., accessible through biometrics authentication. A patient (or authorized medical provider) can access financial data related to the patient's account, in addition to other information system data (pharmacy, laboratory), after being authenticated using the biometrics program 110.

In another embodiment consistent with the present invention, biometrics-linked drug delivery can be performed using the program 110 in a similar manner to the steps shown in FIG. 4. When a new medication is ordered by a physician, a prescription can be delivered to the pharmacy in several ways including paper prescription, fax, electronic transmission, or telephone. Using biometrics, each individual within the drug delivery chain (i.e., pharmacist, ordering physician, and patient) can have documented authentication, which is entered into the EMR for future access. When the patient presents for getting the prescription filled, the biometrics program 110 authenticates the correct identity of the patient and automatically queries the pharmacy information system and EMR to check for potential drug interactions, allergies, and contraindications. The ordering physician's biometrics database can also be queried by the program 110 to ensure the drug being prescribed is appropriate based on the patient's medical disorder (contained within the EMR). Trending analysis can also be performed by the program 110 to ensure the ordering physician is not inappropriately prescribing controlled substances.

In another embodiment consistent with the present invention, different levels of biometrics signatures can be employed by the program 110. For example, the use of biometrics for patient authentication/identification has been well described, and this pertains to biometrics at the "macroscopic" level. Another application of biometrics can be applied at the organ specific level, where a specific organ within a specific patient is authenticated through biometrics. An example of where this may be important is when a patient is undergoing a surgical or interventional procedure (e.g. percutaneous biopsy). In such a case, it is imperative that both the patient and specific organ in question be verified to avoid medical error.

The manner in which this application works is as follows (see FIG. 7).

In step 700, the patient's identity is first established by the program 100 using a biometrics signature as described above.

In step 701, performed at the same time, all personnel associated with the procedure to be performed are also identified and authenticated using the biometrics program 110.

In step 702, the patient's medical database is automatically queried for relevant data by the program 110. In an example, the patient is scheduled for surgical removal of their right kidney due to a malignant mass, identified on abdominal CT.

In step 703, the CT dataset is then retrieved from the database 113 by the program 110, and the specific image highlighting the renal mass along with the radiology report are reviewed and highlighted by the surgeon. Both the imaging data and report have documented a "malignant mass of the right kidney".

In step 704, using existing technology for surgical error proofing, the data from the medical imaging database and intra-operative device are fused to confirm the organ in question corresponds to the pathology in question, the specific laterality of organ pathology (right vs. left) is authenticated, and the patient is authenticated by the program 110 using biometrics in step 705.

In another embodiment consistent with the present invention, biometrics on a "microscopic" or molecular level can be applied to each individual patient's unique DNA genomic analysis, which in turn is authenticated/identified through a biometrics signature by the program 110. This biometrics-linked DNA analysis contains information that can be used by the program 110 to predict a specific patient's predilection to different disease processes (e.g., risk of breast cancer), response to different therapeutic regimens (e.g., specific chemotherapy agents), and cumulative radiation exposure (tied to their disease profile). This "molecular" data is contained within the EMR and accessible through biometrics authentication of the patient and/or treating physician.

Although the above embodiments have been described as different scenarios with different steps, one of ordinary skill in the art would recognize that the steps may be combined between embodiments, and some steps removed or added, or taken in different combinations or orders, in order to achieve the spirit and scope of the invention.

Further, although the medical domain has been described as one application of the present invention, one of ordinary skill in the art would recognize that a number of applications exist for the invention that extends throughout the medical enterprise, as well as for non-medical enterprises. In particular, any situation where high level security is required for identification and/or authentication of personnel involved in the transfer of sensitive information, such as law enforcement; security; insurance; research and product development; banking and investments; legal and judicial; schools; and engineering, would be considered part of the scope of the present invention.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer implemented method of identifying and authenticating an individual for access or privileges, comprising:
   utilizing a biometrics device to obtain biometrics information on the individual;
   recording said biometric information on the individual in a memory of a computerized enterprise system of an enterprise;
   automatically sending said biometrics information from said computerized enterprise system to one of a local, regional, or national computer database for identification;
   forwarding records on the individual from one of said local, regional or national computer database, when matched with said biometrics information, to a visual display device of said computerized enterprise system; and
   allowing access to at least one of said records or said computerized enterprise system when the individual is matched for identity and authenticated;
   displaying an error message when the individual is not matched with said computer database; and
   requesting registration of the biometrics and demographic information of the individual when the individual is not matched or identified.

2. The method according to claim 1, further comprising:
   receiving input regarding the individual into said memory regarding scheduling of a predetermined procedure.

3. The method according to claim 2, further comprising:
   forwarding information on said scheduling to the individual and to the scheduler.

4. The method according to claim 3, further comprising:
   performing a secondary biometrics analysis of the individual at the scheduled time.

5. The method according to claim 4, further comprising:
   confirming said biometrics and demographic information upon completion of said secondary biometrics analysis.

6. The method according to claim 4, further comprising:
   performing editing on at least one of said biometrics or demographic information when said information is not confirmed upon said secondary biometrics analysis.

7. The method according to claim 6, further comprising:
   performing a quality assurance audit of said editing procedure.

8. The method according to claim 6, further comprising:
   performing a third biometrics analysis of the individual after editing is completed.

9. The method according to claim 4, wherein said secondary biometrics analysis is performed at an acquisition device which performs said predetermined procedure.

10. The method according to claim 9, further comprising:
    providing a summary of said procedure and individual demographic information for verification by a predetermined professional.

11. The method according to claim 10, wherein upon verification, a query is forwarded to said local, regional and national computer databases to retrieve relevant records on the individual.

12. The method according to claim 11, further comprising:
    querying said acquisition device for matching records on the individual and said procedure.

13. The method according to claim 12, further comprising:
    confirming said procedure is authorized at said acquisition device and performing said procedure at said acquisition device.

14. The method according to claim 13, further comprising:
    receiving and storing examination data after completion of said procedure; and
    forwarding said examination data to said local, regional and national computer databases.

15. The method according to claim 14, further comprising:
    delivering said examination data to a predetermined list of recipients.

16. The method according to claim 15, wherein the individual approves said list of recipients.

17. The method according to claim 13, wherein said procedure is a radiological procedure.

18. The method according to claim 16, further comprising:
    performing a biometrics analysis at said recipient to allow approved communication to take place between said individual and said recipient.

19. The method according to claim 12, further comprising:
    displaying an error message when records are not found regarding the individual and the procedure; and
    suspending controls on said acquisition device for performance of the procedure on the individual.

20. The method according to claim 19, further comprising:
    establishing the individual's identification to lift said suspension of controls.

21. The method according to claim 19, further comprising:
    initiating a quality assurance audit of the suspension.

22. The method according to claim 2, wherein registration is performed only at predetermined locations.

23. The method according to claim 22, wherein said biometrics and demographic information is forwarded to said one of said local, regional and national computer databases.

24. The method according to claim 23, wherein said local, regional, and national computer databases are cross-checked for accuracy.

25. The method according to claim 2, wherein the biometrics information includes at least two biometric scans on the individual.

26. The method according to claim 25, wherein the biometrics information includes at least one of a fingerprint, palm print, voice recognition, facial recognition, retinal scan, venous flow identification, and electronic signature recognition.

27. The method according to claim 1, wherein the individual is initiating an order.

28. The method according to claim 27, further comprising: receiving an order from said individual.

29. The method according to claim 28, further comprising: cross-referencing said order with said records to confirm privileges or access of said individual are commensurate with said order.

30. The method according to claim 29, further comprising: confirming there are no contraindications to said order by cross-referencing said records.

31. The method according to claim 30, further comprising: initiating a quality assurance audit and denying fulfillment of said order when contraindications are present.

32. The method according to claim 30, further comprising: forwarding said order to a fulfillment department or individual.

33. The method according to claim 32, further comprising: receiving biometrics input of said fulfillment department or individual authorized to fulfill said order.

34. The method according to claim 33, further comprising: tagging said order upon fulfillment; and
receiving biometrics input of said fulfillment individual completing said order.

35. The method according to claim 34, further comprising: receiving biometrics input of a recipient of said order upon receipt of said order.

36. The method according to claim 35, further comprising: notifying said individual and said fulfillment department or individual, that said recipient has received said order.

37. The method according to claim 36, further comprising: recording information related to said order in said memory and said computer databases.

38. The method according to claim 36, further comprising: notifying said ordering individual of said receipt by said recipient of said order.

39. The method according to claim 35, further comprising: initiating a quality assurance audit and denying said order to said recipient when biometrics analysis does not authenticate the recipient.

40. The method according to claim 33, further comprising: initiating a quality assurance audit and denying fulfillment of said order when fulfillment department or individual is not authorized.

41. The method according to claim 32, wherein said order is a prescription and said department or individual is a pharmacy or pharmacist.

42. The method according to claim 32, wherein said order is a surgical procedure, and said department or individual is a surgical center and said individual is a physician.

43. The method according to claim 42, further comprising: performing a biometrics analysis of personnel at said surgical center and of said physician, to authenticate access and privileges to perform said surgical procedure.

44. The method according to claim 43, further comprising: performing a check of said computer databases to ensure there are no contraindications to performing said surgical procedure on said recipient.

45. The method according to claim 44, further comprising: providing a timeout period at said surgical center whereby electronic verification of said surgical procedure is confirmed by personnel at said surgical center and by said physician.

46. The method according to claim 45, further comprising: confirming a surgical site on said recipient; and
authenticating said recipient for said surgical procedure using biometrics analysis.

47. The method according to claim 30, further comprising: recording information related to said order in said memory and said computer databases.

48. The method according to claim 47, further comprising: confirming said order by cross-referencing said order with a biometrics information of a recipient of said order, to ensure no contraindications are present.

49. The method according to claim 48, further comprising: scheduling said order completion date and calendaring said order completion date; and
forwarding said scheduling information to said individual and said recipient.

50. The method according to claim 48, further comprising: checking said order against said computer databases to ensure controlled substances are correctly authorized.

51. The method according to claim 29, further comprising: initiating a quality assurance audit and denying access to said individual when said privileges lack authorization.

52. The method according to claim 27, wherein the individual is one of a patient or a physician, and further comprising:
providing context-specific educational content for the individual to review.

53. The method according to claim 1, wherein said enterprise is one of a school, prison, hospital, law enforcement facility, bank, or court.

54. The method according to claim 1, wherein said biometrics information includes information on the individual's unique DNA genomic analysis, which is authenticated through said records on the individual.

55. The method according to claim 1, further comprising: notifying the individual of scheduling and calendar items when the individual's biometrics is authenticated.

56. The method according to claim 1, further comprising: providing financial data related to the individual's financial accounts when the individual's biometrics is authenticated.

57. An apparatus which provides identification and authentication of an individual such that the individual can gain access or privileges or receive a procedure, at an enterprise, comprising:
a device which allows access and provides a procedure to acquire information on the individual, said device which is connected to or contains a database which stores said information, and said device comprising a display;
a biometrics apparatus which obtains biometrics information on the individual, said biometrics information which is stored in said database;
a communication link which automatically forwards said biometrics information and said information stored in said database, to one of a local, regional, or national database;
means for forwarding records on the individual from one of said local, regional, or national database, when matched with said biometrics information, to said display of said device; and
means for requesting registration of the biometrics and of demographic information of the individual when the individual is not matched or identified,
wherein said biometrics apparatus is integrated within said device; and
wherein said biometrics information is cross-referenced with said database such that when information from said database on the individual matches said biometrics information, said device allows said procedure on, or performs an acquisition on, the individual.

58. The apparatus according to claim 57, wherein the enterprise is one of a school, prison, hospital, law enforcement facility, bank, or court.

59. The apparatus according to claim 57, wherein said device is an imaging device, pharmacy computer, physician computer, or surgical equipment.

60. The apparatus according to claim 57, wherein the biometrics information includes at least one of a fingerprint, palm print, voice recognition, facial recognition, retinal scan, venous flow identification, or electronic signature recognition.

61. The apparatus according to claim 57, wherein said procedure comprises a surgical procedure.

62. The apparatus according to claim 61, wherein said database is checked to ensure that there are no contraindications to performing the surgical procedure on the individual.

* * * * *